United States Patent
Johansen et al.

(10) Patent No.: US 9,798,382 B2
(45) Date of Patent: Oct. 24, 2017

(54) SYSTEMS AND METHODS OF EYE TRACKING DATA ANALYSIS

(71) Applicant: Facebook, Inc., Menlo Park, CA (US)

(72) Inventors: Sune Alstrup Johansen, Copenhagen (DK); Henrik Hegner Tomra Skovsgaard, Copenhagen (DK); Martin Henrik Tall, Frederiksberg (DK); Javier San Agustin Lopez, Copenhagen (DK); Sebastian Sztuk, Copenhagen (DK)

(73) Assignee: Facebook, Inc., Menlo Park, CA (US)

( * ) Notice: Subject to any disclaimer, the term of this patent is extended or adjusted under 35 U.S.C. 154(b) by 0 days.

(21) Appl. No.: 14/254,503

(22) Filed: Apr. 16, 2014

(65) Prior Publication Data
US 2014/0306882 A1   Oct. 16, 2014

Related U.S. Application Data

(60) Provisional application No. 61/812,608, filed on Apr. 16, 2013.

(51) Int. Cl.
G06F 3/01        (2006.01)
G06F 19/00       (2011.01)

(52) U.S. Cl.
CPC ............ *G06F 3/013* (2013.01); *G06F 19/345* (2013.01)

(58) Field of Classification Search
CPC ................................ G06F 3/013; G06F 19/345
See application file for complete search history.

(56) References Cited

U.S. PATENT DOCUMENTS

| | | | |
|---|---|---|---|
| 2006/0189886 A1 | 8/2006 | Jones et al. | |
| 2006/0203197 A1* | 9/2006 | Marshall | A61B 3/112 351/246 |
| 2007/0146637 A1 | 6/2007 | Johnson et al. | |
| 2012/0105486 A1* | 5/2012 | Lankford | G06F 3/013 345/661 |

(Continued)

FOREIGN PATENT DOCUMENTS

| | | |
|---|---|---|
| CN | 105359062 A | 2/2016 |
| WO | WO-2006110472 A2 | 10/2006 |
| WO | WO-2014170760 A2 | 10/2014 |
| WO | WO-2014170760 A3 | 10/2014 |

OTHER PUBLICATIONS

"DynaVox Announces the EyeMax: New Eye Gaze System Provides Greater Independence", [Online]. Retrieved from the Internet: <URL: http://www.dynavoxtech.com/company/press/release/detail.aspx?id=11>, (Aug. 6, 2008), 2 pgs.

(Continued)

*Primary Examiner* — Ryan A Lubit
(74) *Attorney, Agent, or Firm* — Fenwick & West LLP

(57) ABSTRACT

Methods and systems to facilitate eye tracking data analysis are provided. Point of regard information from a first client device of a first user is received, where the point of regard information is determined by the first client device by detecting one or more eye features associated with an eye of the first user. The point of regard information is stored. A request to access the point of regard information is received, and the point of regard information is sent in response to the request, where the point of regard information is used in a subsequent operation.

19 Claims, 13 Drawing Sheets

(56) References Cited

U.S. PATENT DOCUMENTS

| | | | | |
|---|---|---|---|---|
| 2012/0203640 | A1* | 8/2012 | Karmarkar | G06F 1/1686 705/14.66 |
| 2013/0054576 | A1 | 2/2013 | Karmarkar et al. | |
| 2013/0307771 | A1* | 11/2013 | Parker | G06F 3/013 345/158 |
| 2014/0093187 | A1* | 4/2014 | Yehezkel | G06F 17/30274 382/305 |
| 2014/0099623 | A1* | 4/2014 | Amit | G09B 7/00 434/350 |

OTHER PUBLICATIONS

"International Application Serial No. PCT/IB2014/001386, International Preliminary Report on Patentability dated Aug. 26, 2015", 8 pgs.

"International Application Serial No. PCT/IB2014/001386, International Search Report dated Jan. 21, 2015", 4 pgs.

"International Application Serial No. PCT/IB2014/001386, Reponse filed Apr. 21, 2015 to International Search Report and Written Opinion dated Jan. 21, 2015", 29 pgs.

"International Application Serial No. PCT/IB2014/001386, Written Opinion dated Jan. 21, 2015", 7 pgs.

"International Application Serial No. PCT/IB2014/001386, Written Opinion dated Jun. 19, 2015", 7 pgs.

Oyekoya, O K, et al., "Eye tracking—a new interface for visual exploration", BT Technology Journal, Springer vol. 24, No. 3, (Jul. 2006), 57-66.

"Chinese Application Serial No. 201480034281.0, Voluntary Amendment filed May 27, 2016", W/ English Claims, 8 pgs.

"European Application Serial No. 14755706.0, Preliminary Amendment filed Jun. 7, 2016", 22 pgs.

\* cited by examiner

SYSTEMS AND METHODS OF EYE TRACKING DATA ANALYSIS

CROSS-REFERENCE TO RELATED APPLICATIONS

This application claims a priority benefit of U.S. Provisional Application No. 61/812,608, filed Apr. 16, 2013, entitled "Systems and Methods of Eye Tracking Data Analysis," which is incorporated herein by reference in its entirety.

TECHNICAL FIELD

The present disclosure generally relates to computing devices and, more specifically, to systems and methods for facilitating eye tracking data analysis.

BRIEF DESCRIPTION OF THE DRAWINGS

Some embodiments are illustrated by way of example and not of limitation in the figures of the accompanying drawings.

DETAILED DESCRIPTION

Example systems and methods to facilitate eye tracking data analysis are described. In the following description, for purposes of explanation, numerous specific details are set forth in order to provide a thorough understanding of example embodiments. It will be evident, however, to one skilled in the art that the present technology may be practiced without these specific details.

A user of a computing device may utilize an eye tracking device which tracks the user's eye movement as the user looks at a display of the computing device. An image of the user's eyes and/or face, captured by the eye tracking device on or coupled to the computing device, may be analyzed using computer-vision algorithms, such as, for example, eye tracking algorithms and gaze detection algorithms. For example, the captured images may be processed to extract information relating to features of the user's eyes and/or face. The computing device may then use the extracted information to determine the location of the user's eyes and estimate the location on the display at which the user is looking. For example, the computing device may be able to estimate at which icon on the display the user is looking. The estimation data associated with where the user is looking may be sent over a network to a server where the information may be stored and/or processed. The processing results may be presented on a front-end device through which another user may use the data to perform various analyses associated with eye tracking data collected for various users. For example, the results may be used to perform statistical analyses based on user demographics.

Figure 1:
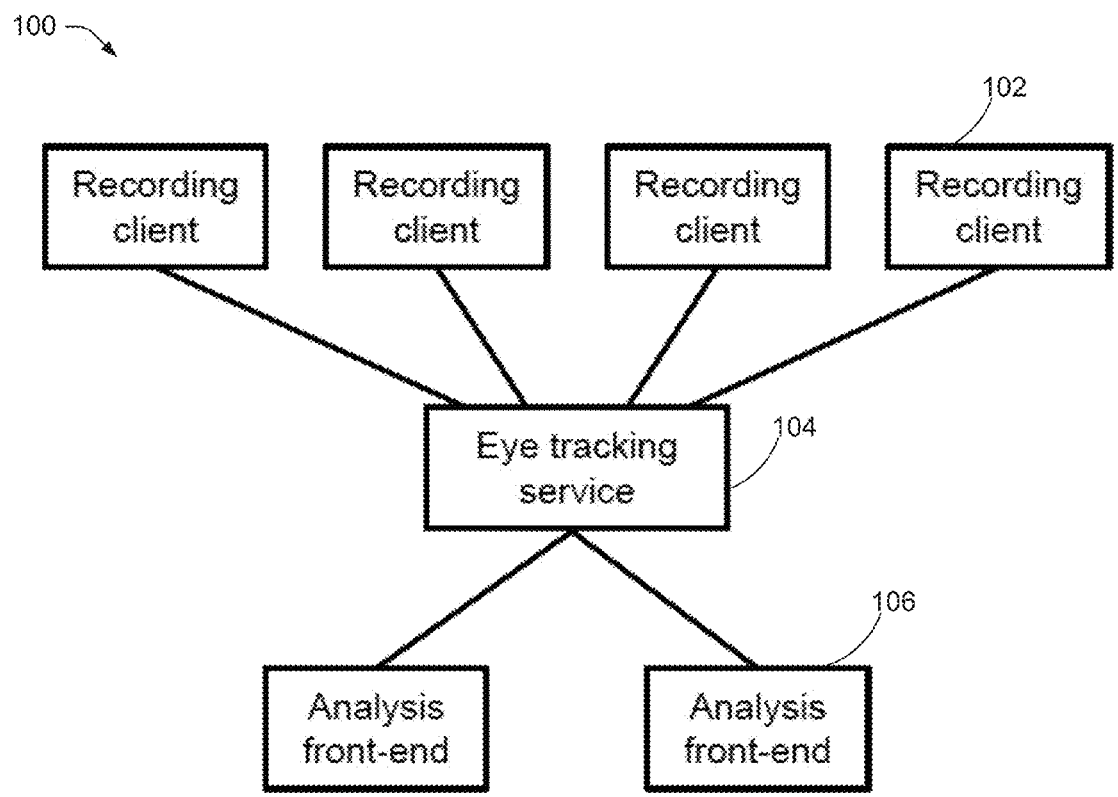
FIG. 1 is a schematic diagram of an example system for eye tracking data analysis, according to some embodiments.

FIG. 1 is a schematic diagram of an example system 100 for eye tracking data analysis. The system 100 includes any number of recording client devices 102, an eye tracking data service 104, and any number of analysis front-end devices 106. The components of the system 100 may be connected directly or over a network, which may be any suitable network. In various embodiments, one or more portions of the network may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or any other type of network, or a combination of two or more such networks.

The recording client device 102 may be any computing device (e.g., laptop, desktop, tablet, smartphone, etc.) capable of collecting, generating, and sending eye tracking data associated with a user of the recording client device 102. The eye tracking data may be sent to the eye tracking data service 104. In some embodiments, if the recording client device 102 is offline, the eye tracking data may be stored at the recording client device 102 and sent to the eye tracking data service 104 when the recording client device 102 is online. Eye tracking data may include any data received from a user (e.g., mouse inputs, keyboard inputs, game controller inputs, screen capture, biosignal inputs, etc.) as well as any data associated with the user's gaze as the user views a display of the recording client device 102. For example, the eye tracking data may include x, y coordinates of a location on the display at which the user was looking. In some embodiments, the recording client device 102 may collect eye tracking data while the user performs a task on the recording client device 102. For example, the recording client device 102 may collect eye tracking data while the user is conducting a task or activity associated with games, printed and online material like television ads, pictures, email marketing, magazines, newspapers, websites, videos, and the like. The eye tracking data may be collected and combined with any other information associated with the user and sent to the eye tracking data service 104.

The eye tracking data service 104 may be a server and/or storage system for creating, recording, and analyzing eye tracking data and any other data sent from the recording client device 102. The eye tracking data service 104 may receive data from distributed groups of persons using the recording client devices 102. In some embodiments, the data received and analyzed may be stored in cloud storage of the eye tracking data service 104. When data arrive from a recording client device 102, the data are stored at the eye tracking data service 104, and eye movement events (e.g., fixations, saccades, glissades, etc.) may be extracted and saved. In some embodiments, the eye tracking data may be reprocessed and saved in order to adjust certain parameters (e.g., level of filtering of the gaze data).

The eye tracking data service 104 may allow users of analysis front-end devices 106 to access data and perform any one or more of the following: create a new study record, upload resources (e.g., images, videos, websites, games, or any other material subject to analysis), view studies and associated resources, save areas of interest (AOIs) for a given resource, request analysis results for a given resource, share one or more studies with other users, and the like. In some embodiments, communicating with the eye tracking data service 104 may require authentication of the user of the analysis front-end device 106 (e.g., username and password). In some embodiments, the eye tracking data service 104 may collect anonymous data of studies created by users as a benchmark database, which may allow users to compare results from their studies with results in the eye tracking data service benchmark database based on any criteria (e.g., geographic location, gender, age, other demographic information of users, etc.) or compare results based on different types of resources (e.g., resources from different industries or market segments). The data stored at the eye tracking data service 104 may be accessed and presented to the user through a user interface (UI) on the analysis front-end device 106. The analysis front-end device 106 may be any computing device (e.g., laptop, desktop, tablet, smartphone, etc.) capable of accessing and presenting the data. A user may view and analyze the data through the UI on the analysis front-end device 106. For example, an analysis of visual attention for any type of visual communication may be performed (e.g., a user may base decisions concerning creative material displayed to a user on results of the analysis). In some embodiments, an application programming interface (API) may allow a user to create, manage, and review studies through the analysis front-end device 106 by uploading content (e.g., resources) to the eye tracking data service 104. In some embodiments, the data may be accessed and analyzed using a web browser on the analysis front-end device 106. The eye tracking data service 104 may host a web service which allows a user of an analysis front-end device 106 to access data and store related analyses. The user may also have the ability to view results using data filters based on any criteria (e.g., geographic location, demographics, etc.); extract, save, and share reports from studies; share studies with other users; compare results from a given study to the benchmark database; and the like.

Users of the recording client devices 102 may also access data managed by the eye tracking data service 104. In some embodiments, communicating with the eye tracking data service 104 may require authentication of the user of the analysis front-end device 106 (e.g., username and password). For example, a user of the recording client device 102 may request studies associated with the user of the recording client device 102, retrieve resources associated with the given studies, send gaze data for a given resource to the service, and the like. In some embodiments, the recording client device 102 may retrieve relevant study information and send eye tracking data to the eye tracking data service 104 for further analysis.

Figure 2A:
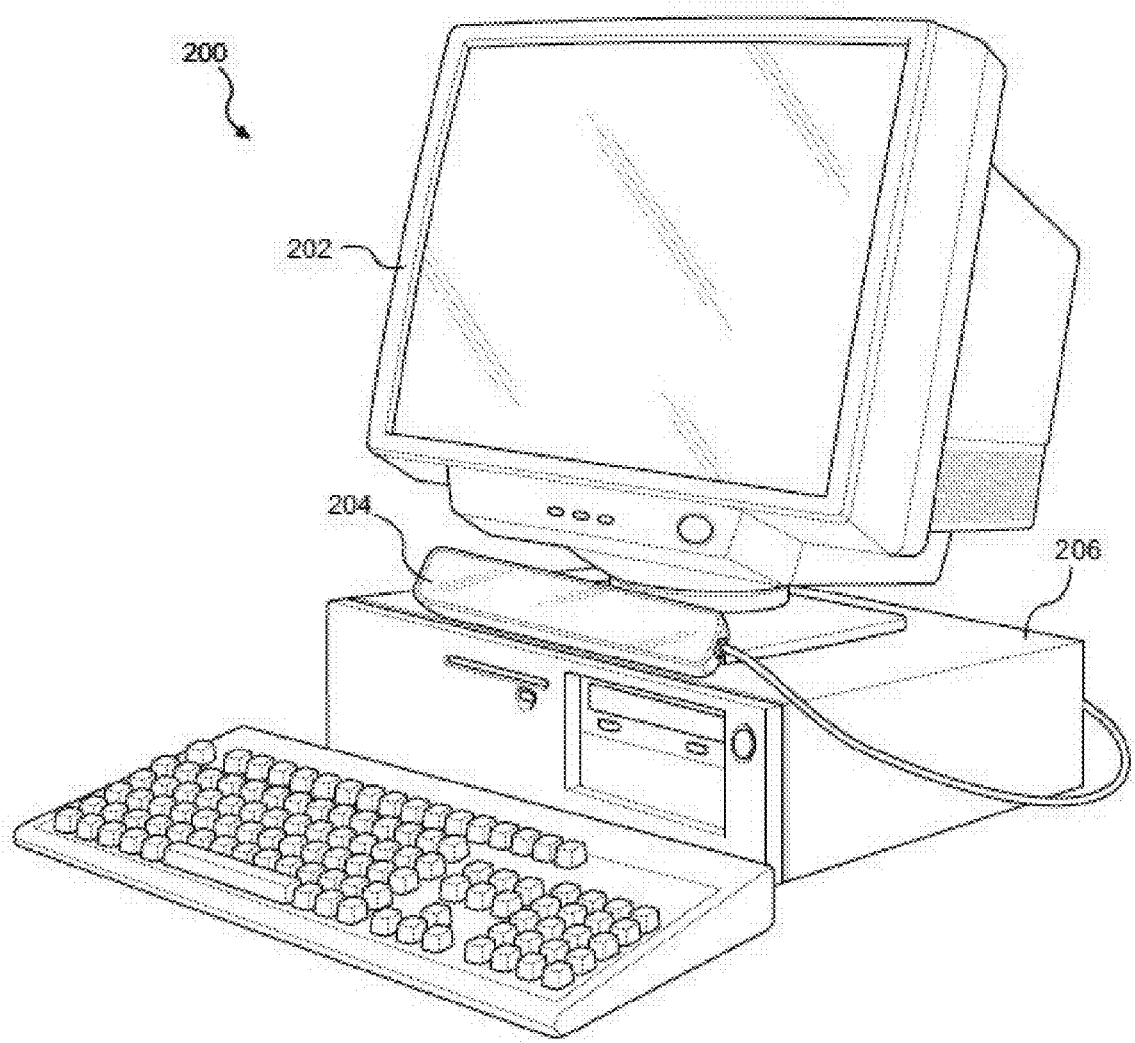
FIGS. 2A-2B are device diagrams of example computing devices coupled to an eye tracking device capable of facilitating eye tracking, according to some embodiments.
Figure 2B:
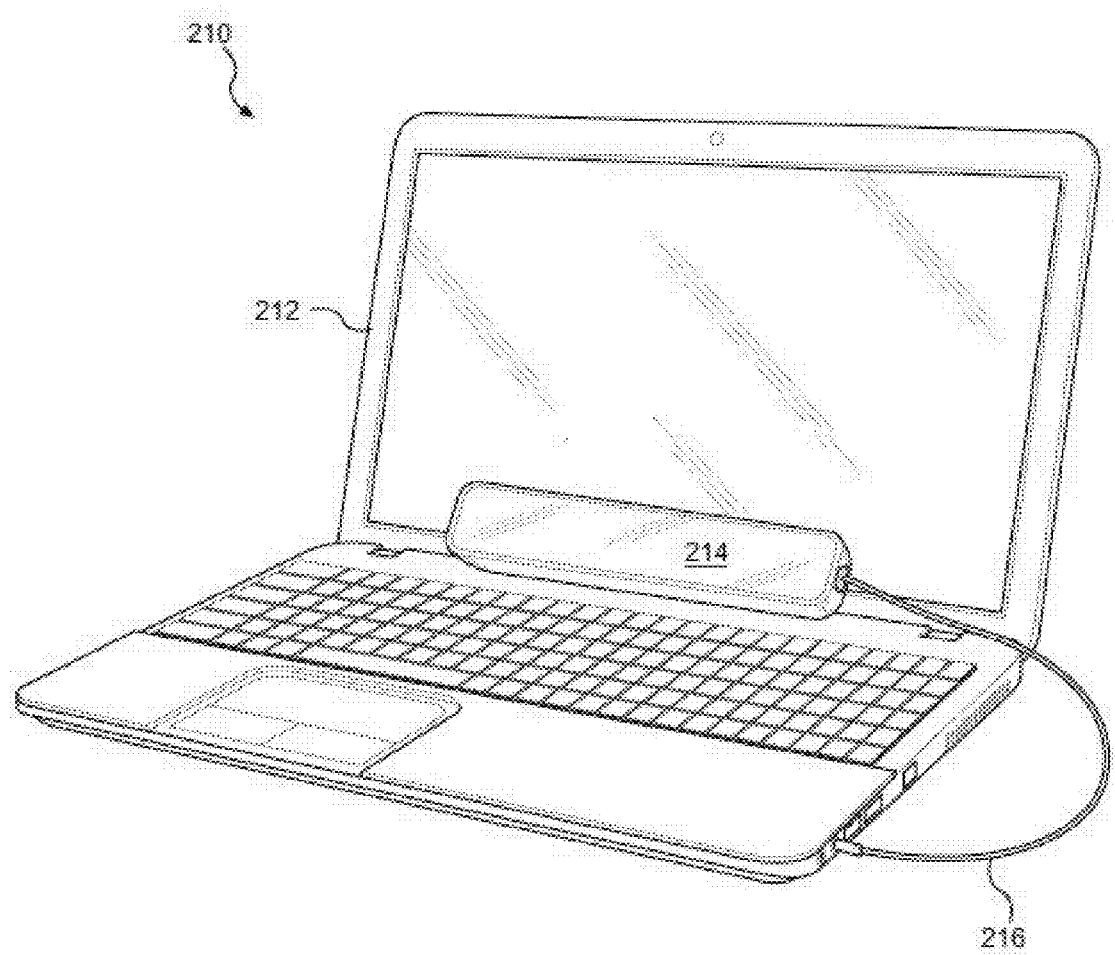

FIGS. 2A-2B are device diagrams of example computing devices coupled to eye tracking devices capable of facilitating eye tracking. In FIG. 2A, the recording client device 200 may include a computing device that is a desktop computing device 202. While a desktop computing device 202 is depicted, one of ordinary skill in the art will appreciate that any type of computing device (smart phone, a personal digital assistant (PDA), a mobile phone, a computing tablet, an electronic reader, a television, a display, etc.) may be used in the recording client device 200. The desktop computing device 202 may be coupled to an eye tracking device 204. The desktop computing device 202 may be coupled to the eye tracking device 204 in any manner, such as through a USB connection 206, for example. The eye tracking device 204 may also be embedded into the desktop computing device 202. The eye tracking device 204 may be capable of capturing eye tracking data, which will be described in more detail below. While the eye tracking device 204 is depicted at the bottom of the display of the desktop computing device 202, one of ordinary skill in the art will appreciate that the eye tracking device 204 may be located at any suitable location relative to the computing device.

FIG. 2B is similar to FIG. 2A but instead depicts a recording client device 210 with a computing device that is a laptop computing device 212. The laptop computing device 212 may be coupled to an eye tracking device 214 in any manner, such as through a USB connection 216. The eye tracking device 214 may also use one or more cameras and/or one or more light sources integrated in the laptop computing device 212.

FIGS. 3A-3G are device diagrams of an example eye tracking device 300 capable of facilitating eye tracking. FIGS. 3A-3G show different perspective views of the eye tracking device 300. As described for FIGS. 2A and 2B, the eye tracking device 300 may be coupled to a computing device of the recording client device in any manner, such as through a USB port on the computing device, micro USB port on the computing device, a proprietary port on the computing device, and the like. The eye tracking device 300 may also be integrated in a computing device (e.g. in the form of a laptop web camera or a front-facing camera in a smartphone or tablet). The eye tracking device 300 may include camera module 302 and one or more light-emitting diodes (LEDs) 304. For explanatory purposes, LEDs 304 are depicted and described throughout the disclosure. However, one of ordinary skill in the art will appreciate that any appropriate light-emitting source may be used (e.g., infrared laser). Additionally, the technology described may be used with other camera configurations that may not include light-emitting sources (e.g., any camera such as a web camera, etc.).

The eye tracking device 300 may include any number of infrared LEDs 304 that may be placed in a suitable location in any manner within the eye tracking device 300 (e.g., tilted at an angle such that it points toward the user's face). In a specific embodiment, the one or more LEDs 304 may be synchronized with the one or more cameras in such a way that the one or more LEDs are on when the one or more cameras are grabbing a frame, and off otherwise.

The camera module 302 may include one or more front-facing cameras placed in any suitable location in any manner within the eye tracking device 300 (e.g., tilted at an angle such that it points toward the user's face) and may be used to capture images of the user's eyes and/or face. The one or more cameras may be placed at an appropriate distance from the LEDs 304 to optimize the proper capture of the infrared light. In some embodiments, a camera on the computing device coupled to the eye tracking device 300 is used in combination with camera module 302 in stereo mode. The camera module 302 may include any one or more of the following: a black and white (e.g., monochrome) or color (e.g., RGB) CMOS sensor, running at an appropriate frame per second rate (e.g., high-definition at 30 frames per second), a lens without an infrared block filter and with an appropriate field of view and depth of field (e.g., approximately 40-120 cm on a desktop scenario, and approximately 2 to 5 meters in a TV scenario), and the like. The one or more cameras in the camera module 302 may be positioned such that the one or more cameras are tilted toward the user's face.

In some embodiments, the eye tracking device 300 may also include a suitable type of infrared pass filter (e.g., active, mechanical, high-pass, band-pass, etc.). In some embodiments, a high-pass filter that blocks light below 800 nm and allows light above 800 nm is used. In some embodiments, the infrared pass filter may only allow light between 800-900 nm to enter the one or more cameras of the camera module 302.

The images captured by the camera may need to be rotated. The eye tracking software can use sensors on the computing device (e.g., accelerometer, magnetometer, etc.) to detect the orientation of the computing device and rotate the image accordingly so that it can be properly processed.

The eye tracking device 300 may also include an electronic circuit board with the LEDs 304 and the one or more cameras. The electronic circuit board may also include any one or more of the following: electronic components (e.g., resistors, capacitors, coils), connectors (e.g., female micro-USB connector, JST 5-pin USB connector), and the like. In some embodiments, the eye tracking device 300 may also include a connector cable that powers the LEDs 304 and the camera module 302 and allows data transfer between the eye tracking device 300 and the computing device.

In some embodiments, the eye tracking device 300 may also include weights toward the back of the eye tracking device 300 to allow the eye tracking device 300 to stay in a tilted position. The eye tracking device 300 may also include stabilizing components 306 which may increase friction and allow the eye tracking device 300 to lean against one or more components of the computing device (e.g., against the screen of a laptop). Additionally, a thread component 308 may be included in the eye tracking device 300, which may fit in the standard ¼ inch camera stand or tripod.

Figure 3A:
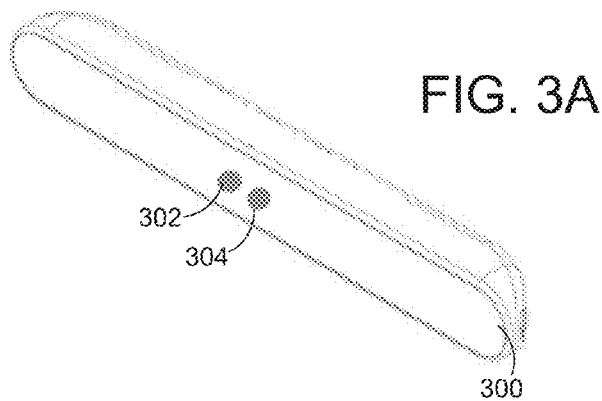
FIGS. 3A-3G are device diagrams of example eye tracking devices capable of facilitating eye tracking, according to some embodiments.
Figure 3B:
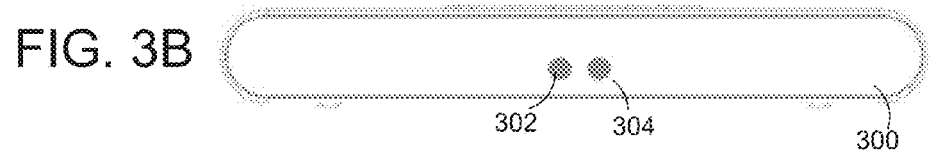
Figure 3C:
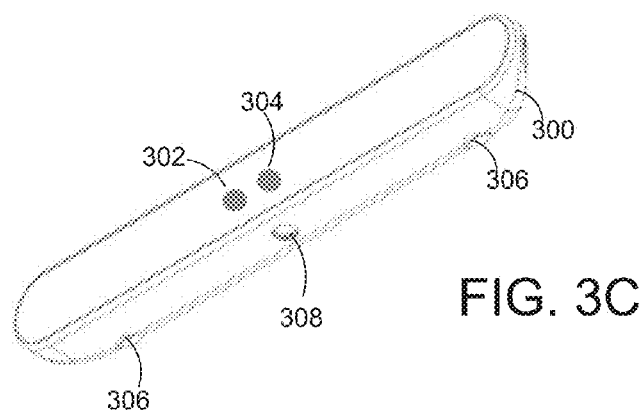
Figure 3D:
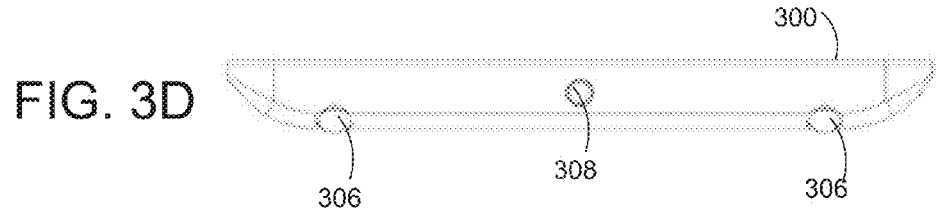
Figure 3E:
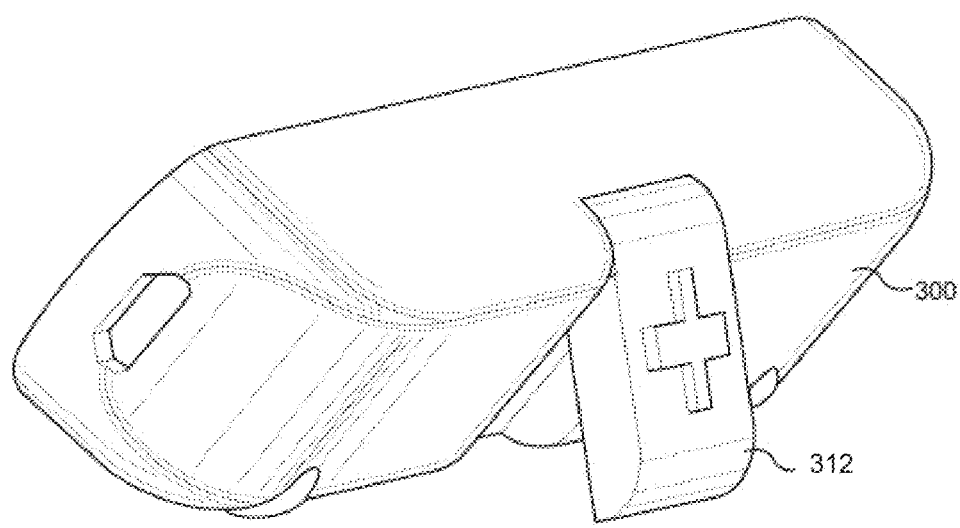
Figure 3F:
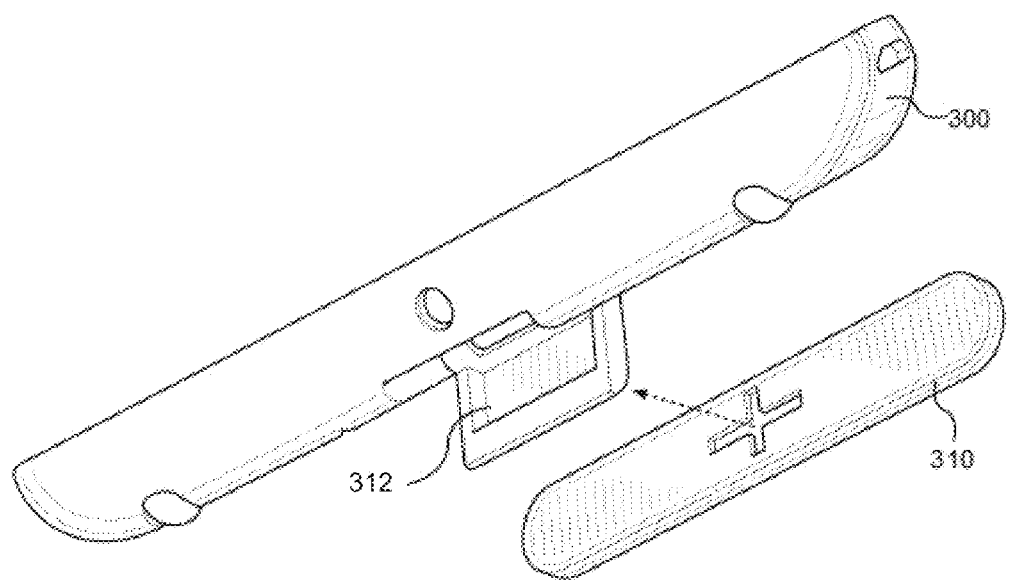
Figure 3G:
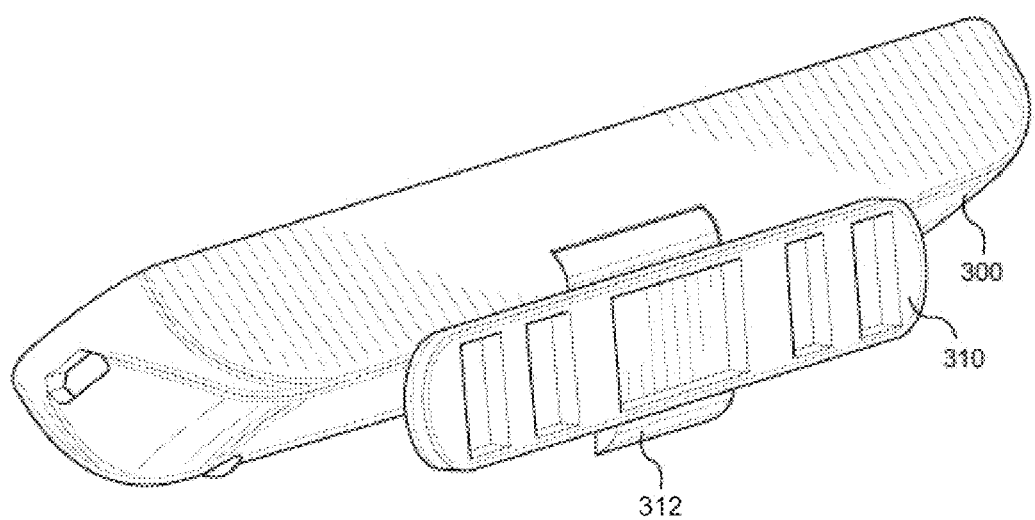

Additionally, a stand with a hinge for a monitor may be used and/or included with the eye tracking device 300, allowing the eye tracking device 300 to lean at different angles. An example of this is shown in FIGS. 3E-3G. In some embodiments, the leg 312 of the eye tracking device 300 may contain metal pieces fastened to the inside of the leg 312. A hinge device 310 may attach to a display device in any manner, such as through the user of magnets, glue, a hinge that fits to the screen, and the like. In some embodiments, the hinge device 310 may contain one or more magnets that may attach with the leg 312 of the eye tracking device 300, thereby making it possible to easily attach and detach the eye tracking device 300 from the display device while leaving the hinge device 310 fastened to the display device if desired. The hinge device 310 may also be configured so that the hinge device 310 may be unfastened from the display device as well. In some embodiments, the one or more magnets attaching the eye tracking device 300 to the display device may also be the same one or more magnets attaching the leg 312 to the display device. In some embodiments, the one or more magnets may be built into the eye tracking device 300 so that the eye tracking device 300 may be affixed on the display device. The hinge device 310 and the leg 312 may have a geometry such that the hinge device 310 and the leg 312 fit together so that the eye tracking device 300 is properly and firmly placed. The hinge device 310 may allow the eye tracking device 300 to be fastened to the display device and adjusted so that it points toward the user (e.g., toward the user's eyes).

The LEDs 304 emit light that is focused and centered toward the eyes of the user. The infrared light from the LEDs 304 is reflected in the pupil and on the cornea of the user and recorded by the cameras in the camera module 302. The LEDs 304 may be synchronized with the one or more cameras so that the LEDs 304 are on only when the one or more cameras are grabbing an image. In some embodiments, to improve the image quality, visible light below 800 nm is filtered out using an infrared pass filter. The field of view and depth of view of the lenses of the one or more cameras in the camera module 302 may allow the user to move around, thereby accommodating for head pose variance of the user. The eye tracking control software may analyze the images taken by the camera module 302 to provide eye tracking data, such as x,y coordinates of where the user is looking on the display of the computing device, location of the user in 3-D space, pupil dilation, blink rates, and the like.

The LEDs 304 and the camera module 302 may be turned on and/or off in any manner, such as by utilizing an external slider, an on-off dedicated button on either the computing device or the eye tracking device 300, controlled by an application or a digital button on the screen, controlled by movement or shaking of the computing device and/or the eye tracking device 300, controlled by voice commands, on-screen capacitive buttons, touch pad(s), bio-signals (e.g., EMG, EEG, etc.) and the like. As such, in some embodiments, the eye tracking components may consume power only while the LEDs 304 and the camera are turned on (e.g., when the user is using the eye tracking features). In some embodiments, the LEDs 304 and the camera may be turned off when the user's face or eyes are not detected for a predetermined amount of time (e.g., 5-10 seconds) and may turn on again when the user's face or eyes are detected.

Figure 4:
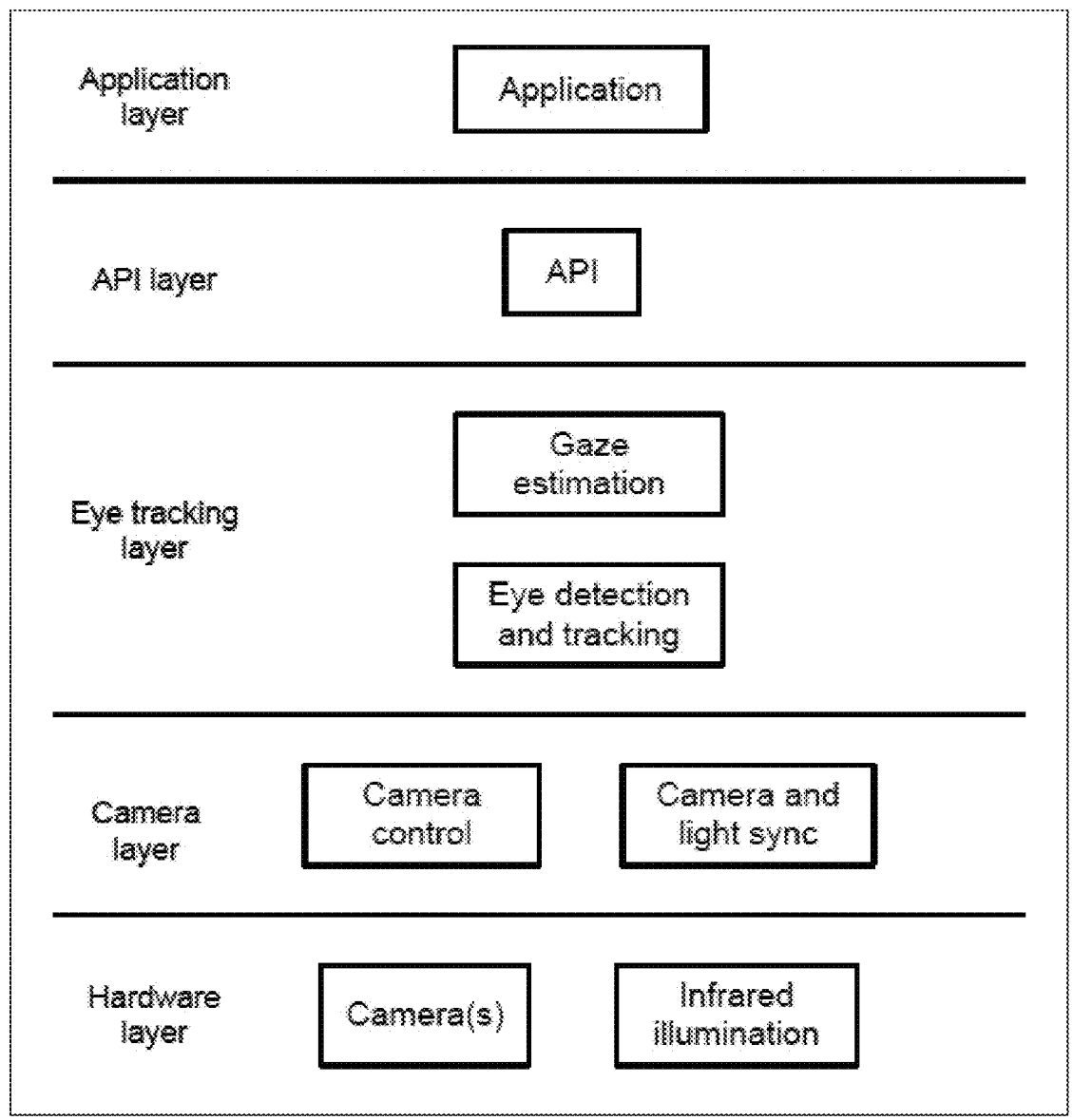
FIG. 4 is a block diagram of an example software architecture for facilitating eye tracking, according to some embodiments.

FIG. 4 is a block diagram of an example software architecture for facilitating eye tracking. Any one or more of the components of the software architecture may run on either a control processing unit (CPU) of the computing device of the recording client device or on a combination of a CPU and a graphics processing unit (GPU) of the computing device. In some embodiments, any one or more of the components of the software architecture may run on a dedicated chip. The software may run as a background process (e.g., as part of the operating system (OS)) or as part of another application already running on the device (e.g., a web browser), and may provide an application programming interface (API) that other applications can access. The API may fire an event or use some other similar mechanism to send the information of where the user is looking on the screen to other applications.

The software architecture may be divided into different layers. The bottom layer would correspond to the hardware (e.g., the camera(s), the infrared illumination, etc.). A camera layer may be in charge of communicating with the camera(s) in order to perform camera operations such as, for example, starting the camera, grabbing images, controlling the camera properties, and the like. This layer may also synchronize the one or more cameras and the infrared emitters so that the lights are only on when there is an image being captured and off the rest of the time (e.g., strobing).

The camera layer may deliver images to the eye tracking layer. In the eye tracking layer, images may be processed to find features like face location, eye region location, pupil center, pupil size, location of the corneal reflections, eye corners, iris center, iris size, and the like. These features are used in the gaze estimation stage, which may be in charge of calculating the point of regard of the user, which may be the location on the display where the user is looking. The gaze estimation stage may also calculate the optical and visual axes of the user's eyes.

The API layer may be used for communication between the eye tracking layer and applications that use eye gaze information (e.g., OS API, games that employ eye gaze information, applications for sending eye tracking data to the eye tracking data service, etc.). The API may send eye tracking data calculated by the eye tracking layer, such as coordinates of the point of regard, three-dimensional (3-D) location of the user's eyes, pupil size, and the like. The API may also accept commands from an application to the eye tracking layer (e.g., to start and/or stop the eye tracking engine, query for specific information, etc.). An application may connect to the eye tracker's API and use eye gaze information for any suitable purpose (e.g., record eye data for visual behavior studies).

In some embodiments, an application on the recording client device may be used to access eye tracking data analysis features. The user may log in using the recording client device application to access data available on the eye tracking data service, such as a list of studies that are available for the user to participate in, and the like. The user may also begin collecting data for a study using the recording client device application. In some embodiments, the recording client device application may display a window with a silhouette of a face overlaid on the image stream captured by the one or more cameras in order to help the user place the user's head or the device such that the user's face is displayed within the boundaries of the face silhouette. The recording client device application may inform the user when the face is correctly placed. In some embodiments, the recording client device application may show this feedback before and/or during a study.

The recording client device application may present the user with a calibration window followed by a sequence of resources (e.g., images, videos, websites, and the like), in a specific or in a random order, that the user may observe. The recording client device application may collect data during the time the user is observing each resource. The recording client device application may display a calibration window after one or more resources have been display in order to measure the accuracy of the eye tracking software and/or recalculate the calibration parameters. The recording client device application may run as a stand-alone application or may run inside another application (e.g., in a browser).

In some embodiments, the recording client device may offer eye control to the user for various applications (e.g., games). For example, using eye tracking data, a user may control the scrolling of a page displayed in a browser as the user reads (e.g., automatic scrolling as the user reads and approaches the bottom of the page), a game may offer some type of eye control feature, and the like. These various applications may use eye tracking data to enable eye control in the applications. This eye tracking data may also be collected and sent to the eye tracking data service for any future analysis. The collected data may be analyzed for any purpose. For example, if the data is collected while a user is playing a game, the analysis of the data may be used to improve the design of the game. In the example of data analysis for a game, a game developer may analyze the data and determine whether users saw a particular piece of information provided to the user, the percentage of users that notice a particular game element or character in the game, the amount of time users spent looking at a particular element, the order in which the attention falls on different elements on the screen, and the like. In an example in which data is analyzed for marketing purposes, a market researcher may analyze the data to determine information such as the percentage of users that saw a specific advertisement while reading a website or while playing a game, a comparison of "seen" rate versus click-through rate for an advertisement, and the like. In some embodiments, the eye tracking data sent may be anonymized.

In some embodiments, the recording client device application may present a calibration window after one or more resources have been presented to the user. The calibration window may consist of one or more calibration points displayed on the screen. The recording client device application may calculate the accuracy of the existing user calibration and/or recalculate the user calibration parameters in order to improve the accuracy. The recording client may use the accuracy calculated in one or more calibration windows to assign an accuracy value for one or more resources. The accuracy value may be used by an analysis tool in order to filter results on data collected from one or more users.

Figure 5:
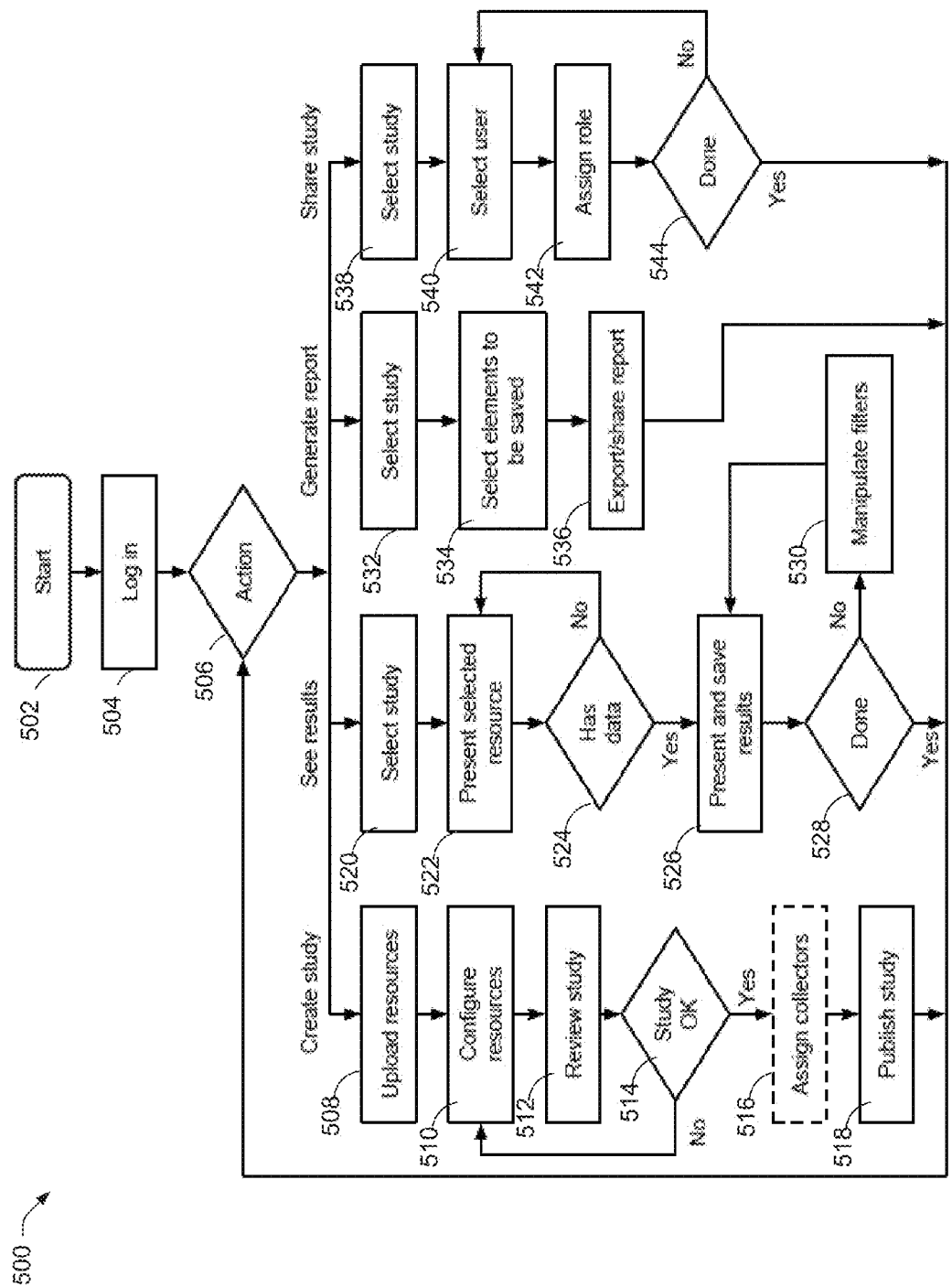
FIG. 5 is a flowchart of an example method of utilizing eye tracking data, according to some embodiments.

FIG. 5 is a flowchart of an example method 500 of utilizing eye tracking data. The method 500 may be performed by the analysis front-end device 106 depicted in FIG. 1. In operation 502, the analysis front-end device 106 may initiate access to data for analysis through an analysis application (e.g., when the UI or web service is launched).

In operation 504, the analysis application may request that the user be authenticated. In some embodiments, this may include logging into an account on the analysis application using user credentials (e.g., username and password).

In operation 506, once the user is authenticated, the user may select an action to take. Any number of options for actions to take may be available to a user, including creating a study, viewing results, generating a report, sharing a study, and the like.

In operation 508, if the user chooses to create a study, the user may upload resources relating to the study. The resources may be uploaded to the analysis application. The user may also provide a URL or a URI that points to the location where the resource is hosted.

In operation 510, the analysis application may configure the resources.

In operation 512, the analysis application may present the study to the user and allow the user to review the study.

In operation 514, the user may input an indication of whether the user approves of the study. If the user does not approve of the study, operations 510 and 512 may be repeated until the user approves.

In operation 516, if the user approves of the study, the user may have the option to assign collectors to the study, which may be entities who may collect data associated with the study.

In operation 518, the study may be published. Once the study has been created and published, the user may have the option of selecting another option in operation 506.

In operation 520, if the user chooses to view results of a study, the user may select a study to view.

In operation 522, the analysis application may present the selected resource.

In operation 524, the analysis application checks whether there is eye tracking data associated with the selected resource. If there is no eye tracking data associated with the resource, operation 522 may be repeated.

In operation 526, if there is eye tracking data associated with the resource, the selected results are displayed. For example, a heat map may be displayed overlaid on the resource to illustrate what areas of the resource have attracted most visual attention. The user may save the results for later analysis.

In operation 528, the user may select whether the user is finished viewing the data. If the user is finished viewing the data, the user may have the option of selecting another option in operation 506.

In operation 530, if the user is not finished viewing the data, the user may be given the option to further manipulate filters for the data (e.g., select another demographic segment, modify the age range, filter on a minimum accuracy, etc.). The data may then be presented and saved in operation 526.

In operation 532, if the user chooses to generate a report, the user may be given the option to select a study associated with the report the user wishes to generate.

In operation 534, the user may select elements of the study the user wishes to include in the report and save.

In operation 536, the report may be generated based on the selected elements of the selected study and exported and/or shared. Once the user has generated the report, the user may have the option of selecting another option in operation 506.

In operation 538, if the user chooses to share a study, the user may select the study the user wishes to share.

In operation 540, the user may select another user with whom the user wishes to share the study.

In operation 542, the user may assign a role to the other user with whom the study is to be shared.

In operation 544, the analysis application may determine whether the user has indicated that the user is finished sharing the study. If not, the user may select, in operation 540, yet another user with whom to share the study. If the user is finished sharing the study, the user may have the option of selecting another option in operation 506.

Figure 6A:
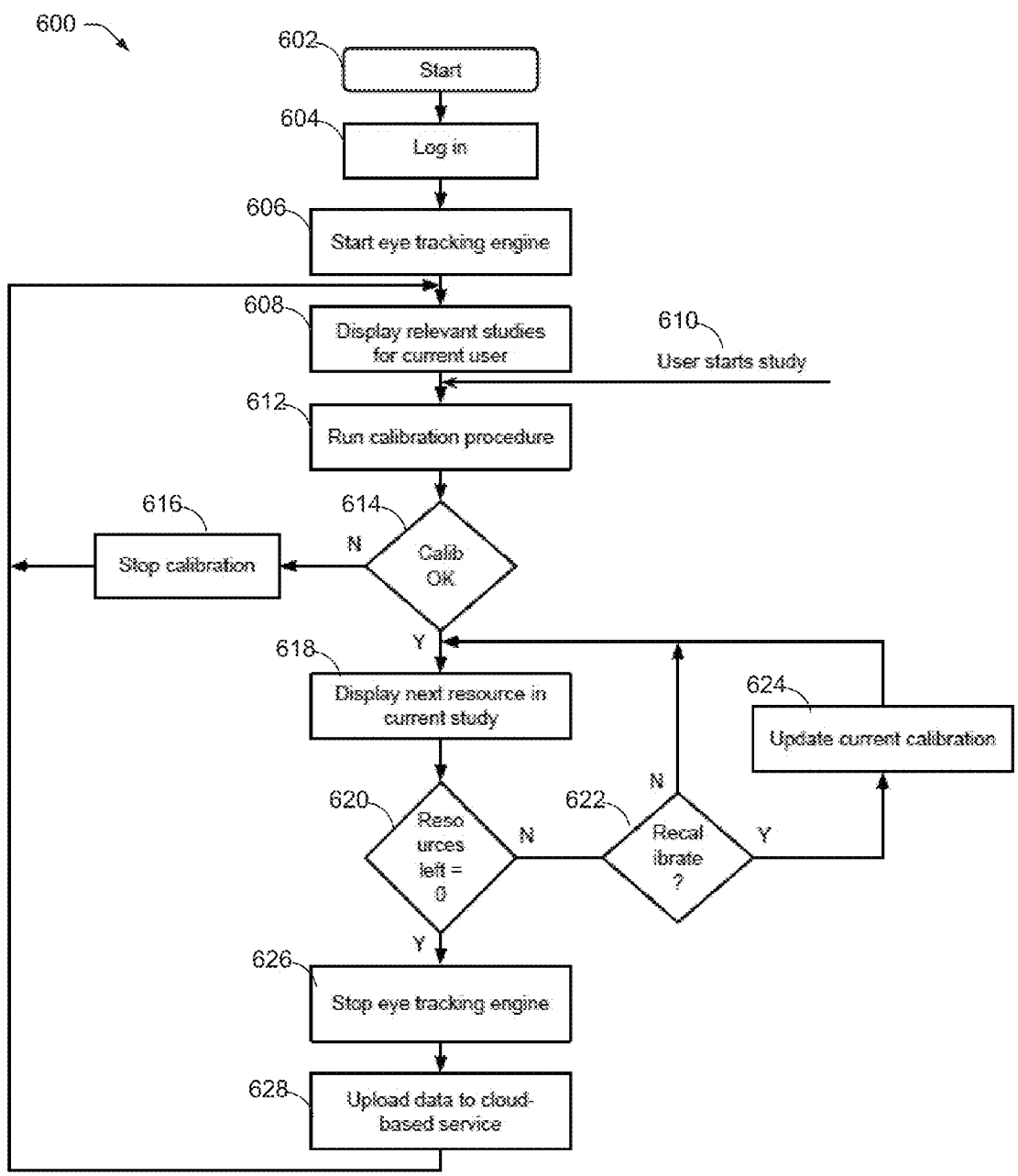
FIGS. 6A-6B are flowcharts of example methods of collecting and transmitting eye tracking data, according to some embodiments.
Figure 6B:
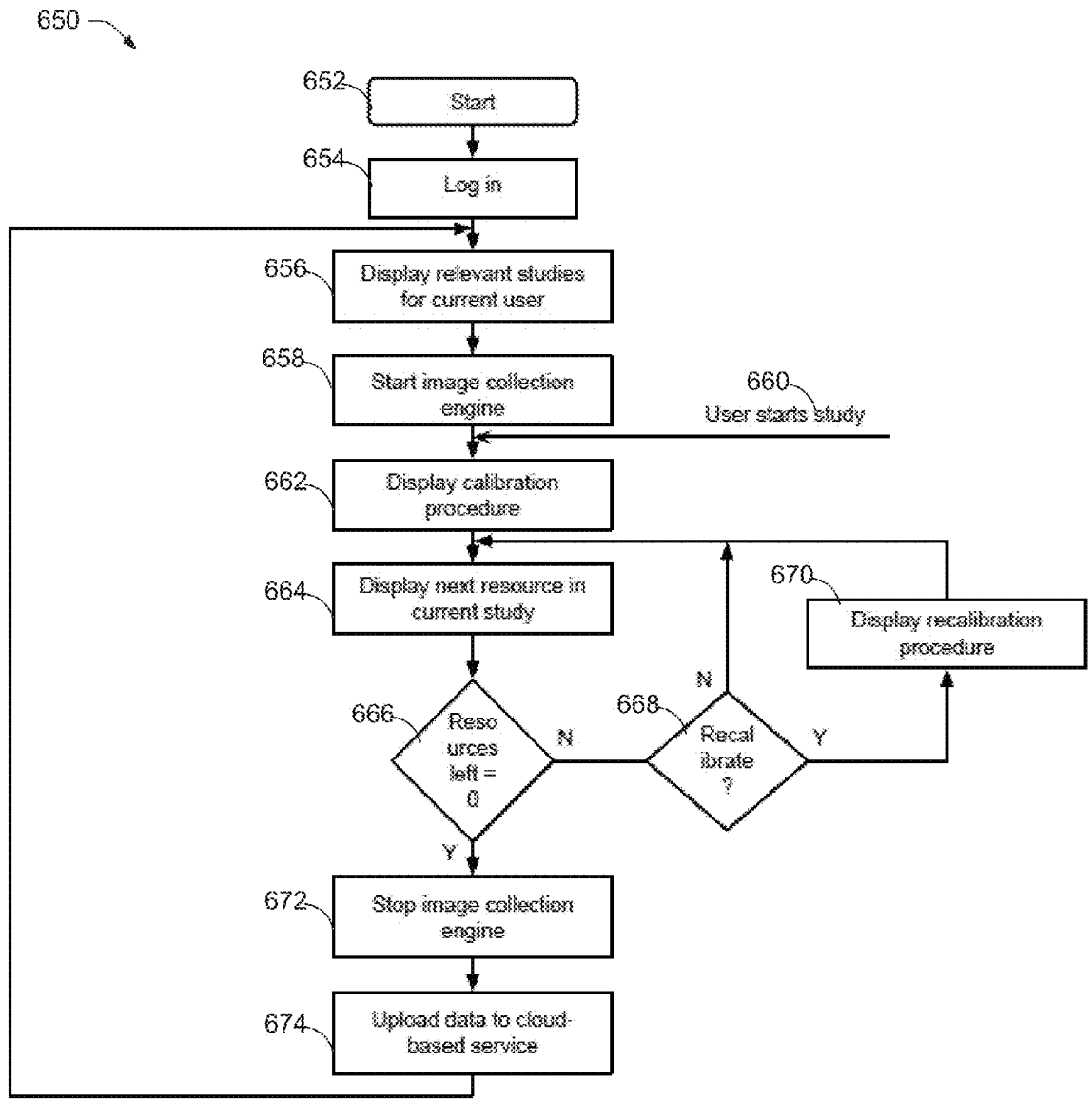

FIGS. 6A-6B are flowcharts of example methods of collecting and transmitting eye tracking data. The methods 600 and 650 of FIGS. 6A and 6B, respectively, may be performed by the recording client device 102 depicted in FIG. 1.

In operation 602 of the method 600 of FIG. 6A, the recording client device 102 may initiate eye tracking (e.g., when a user launches an application or a web service in a browser).

In operation 604, the application may request that the user of the recording client device 102 be authenticated. In some embodiments, this may include logging into an account on the analysis application using user credentials (e.g., username and password).

In operation 606, once the user has been authenticated, the application may launch the eye tracking engine (e.g., eye tracking layer described for FIG. 4).

In operation 608, the application may display relevant studies for the user.

In operation 610, the user may begin the study (e.g., conducting a task or activity associated with games, printed and online material like television ads, pictures, email marketing, magazines, newspapers, websites, videos, etc.).

In operation 612, a calibration procedure may begin running to calibrate the eye tracking device to the user. In some embodiments, the calibration procedure may not be necessary if a previous calibration for the user exists.

In operation 614, the application may determine whether the eye tracking device has been calibrated.

In operation 616, if the calibration is insufficient, the calibration process may stop and operation 608 may begin again.

In operation 618, if the calibration is sufficient, the next resource for the current study may be displayed.

In operation 620, the application may determine whether there are any resources left in the current study.

In operation 622, if there are resources remaining, the application may determine whether the eye tracking device should be recalibrated and/or whether the calibration accuracy should be calculated. If not, the next resource may be displayed (operation 618). If the eye tracking device should be recalibrated, in operation 624, the current calibration may be updated, and the next resources may be displayed (operation 618).

In operation 626, if there are no resources left, the eye tracking engine stops, and in operation 628, the data collected during the study (e.g., mouse data, eye gaze data, eye gaze accuracy results, other biometric data) are uploaded to the eye tracking data service. The application may then display other relevant remaining studies for the user (operation 608).

FIG. 6B depicts a method 650 of collecting and transmitting eye tracking data. The method 650 is similar to the method 600 of FIG. 6A. However, the method 650 uploads images taken by the one or more cameras or portions of these images to the eye tracking data service for processing, instead of processing the images locally on the recording client device 102.

In operation 652, the recording client device 102 may initiate eye tracking (e.g., when a user launches an application or a web service in a browser).

In operation 654, the application may request that the user of the recording client device 102 be authenticated. In some embodiments, this may include logging into an account on the analysis application using user credentials (e.g., username and password).

In operation 656, once the user has been authenticated, the application may display relevant studies for the user.

In operation 658, the application may start the image collection engine to collect images of the user.

In operation 660, the user may begin the study (e.g., conducting a task or activity associated with games, printed and online material like television ads, pictures, email marketing, magazines, newspapers, websites, videos, etc.).

In operation 662, the calibration procedure may be displayed to the user.

In operation 664, the next resource in the study may be displayed to the user.

In operation 666, the application may determine whether there are any resources left.

In operation 668, if there are resources remaining, the application determines whether the eye tracking device should be recalibrated and/or whether the calibration accuracy should be computed. If not, the next resource may be displayed (operation 664). If the eye tracking device should be recalibrated, in operation 670, the current calibration is updated, and the next resources may be displayed (operation 664).

In operation 672, if there are no resources left, the image collection engine stops, and in operation 674, the images and data collected during the study (e.g., mouse data, other biometric data) are uploaded to the eye tracking data service. The application may then display other relevant remaining studies for the user (operation 656).

Figure 7A:
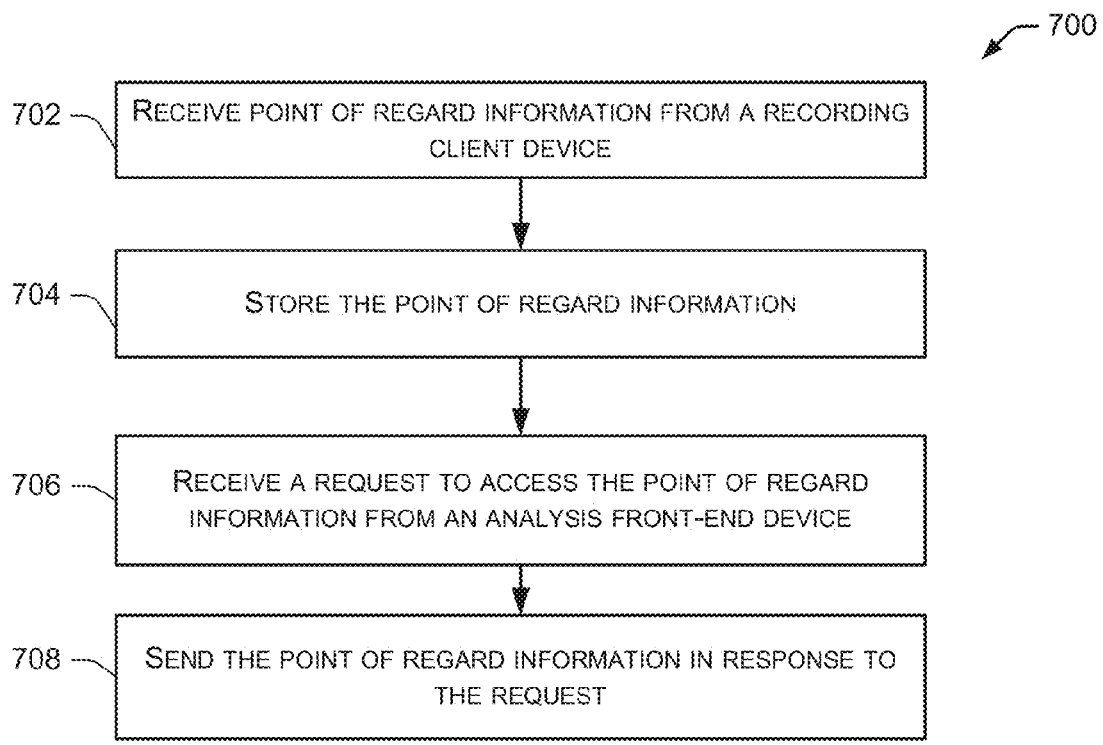
FIGS. 7A-7C are flowcharts of example methods of performing eye tracking data analysis, according to some embodiments.
Figure 7B:
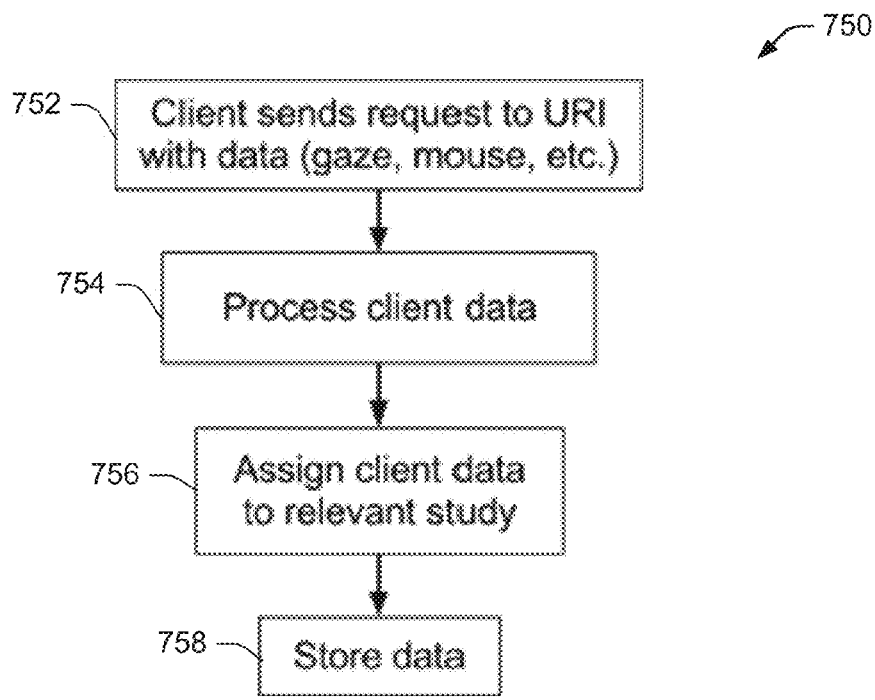
Figure 7C:
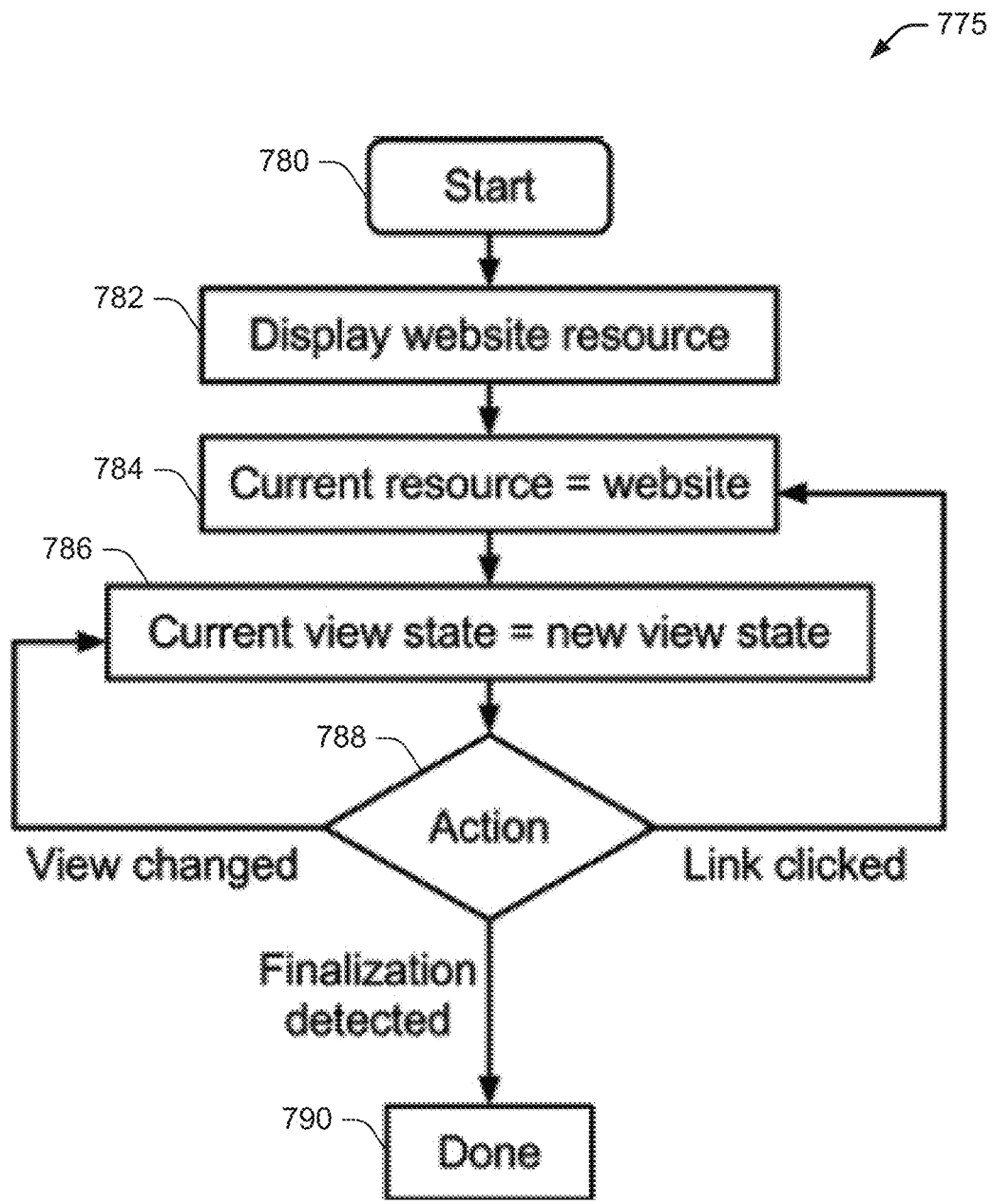

FIGS. 7A-7C are flowcharts of example methods of performing eye tracking data analysis. In operation 702 of the method 700 depicted in FIG. 7A, the eye tracking data service may receive point of regard information from a recording client device. Additionally, the eye tracking data service may receive any additional information from the recording client device, such as face location and orientation, eye region location, pupil center, pupil size, location of the corneal reflections, eye corners, iris center, iris size, screen captures, mouse cursor data, keyboard data, game controller data, heart rate data, biometric data, and the like.

In operation 704, the eye tracking data service may store the point of regard information and any additional information received from the recording client device.

In operation 706, the eye tracking data service may receive a request to access the point of regard information (or any additional information stored at the eye tracking data service) from an analysis front-end device.

In operation 708, the eye tracking data service may send the point of regard information (or any additional information stored at the eye tracking data service) to the analysis front-end device in response to the request.

FIG. 7B is a flowchart of another example method 750 of performing eye tracking data analysis. In operation 752, a recording client device may send a request to the eye tracking data service through a uniform resource identifier (URI). The request may be sent with eye tracking data and any additional user-related data (e.g., mouse inputs, screen captures, biometric data, etc.).

In operation 754, the eye tracking data service may process the received data. This may include parsing the data and extracting any information to be stored (e.g., fixations, saccades, eye blinks, click events, biosignal activations, etc.).

In operation 756, the eye tracking data service may assign the data received from the recording client device and the extracted data to the corresponding study for which the user collected information.

In operation 758, the data received from the recording client device, the extracted data, and the assignment may be stored at the eye tracking data service.

Recording eye tracking data for website resources differs from static resources such as images and video due to the inherent dynamic properties of the interactive elements and changes of the URI. Website resources may have content that changes by user input, event-driven actions, and the like (e.g., activating a drop-down menu, system notifications, clicking on a link, etc.). The recorded data may be mapped to the changes in the displayed content for better results in the analysis section of the system 100. In order to accommodate for the dynamic behavior, the recording client may detect and register any changes on the display while presenting website resources. This may allow the recording client to map recorded data to the different presented displays.

In some embodiments, introducing view states to discriminate recorded eye-tracking data to the displayed content can be used. That is, whenever the displayed content of a website resource is changing, the recording client device 102 may map the recorded data to the current view state. The use of view states may allow the system 100 to allow for analyzing the observed view states from any presented website resource separately or in any desired combinations.

FIG. 7C is a flowchart of an example method 775 of recording data for a resource with dynamic data, such as a website. In the presented example, it is assumed that the eye tracking engine is running and data are being recorded when the method 775 begins at operation 780.

In operation 782, the application displays a web site resource.

In operation 784, the current resource refers to the displayed website.

In operation 786, the current view state is set as a new view state.

In operation 788, a change in the view may be detected and the current view state is may be updated at operation 786, or a link may be clicked and the current resource may be updated at operation 784, or if a finalization event has been detected the display of the website resource may be done at operation 790.

Certain embodiments are described herein as including logic or a number of components, modules, or mechanisms. Modules may constitute either software modules (e.g., code embodied on a machine-readable medium or in a transmission signal) or hardware modules. A hardware module is a tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation, and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., Application Program Interfaces (APIs)).

Example embodiments may be implemented in digital electronic circuitry, or in computer hardware, firmware, software, or in combinations of them. Example embodiments may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., a FPGA or an ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that that both hardware and software architectures merit consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Figure 8:
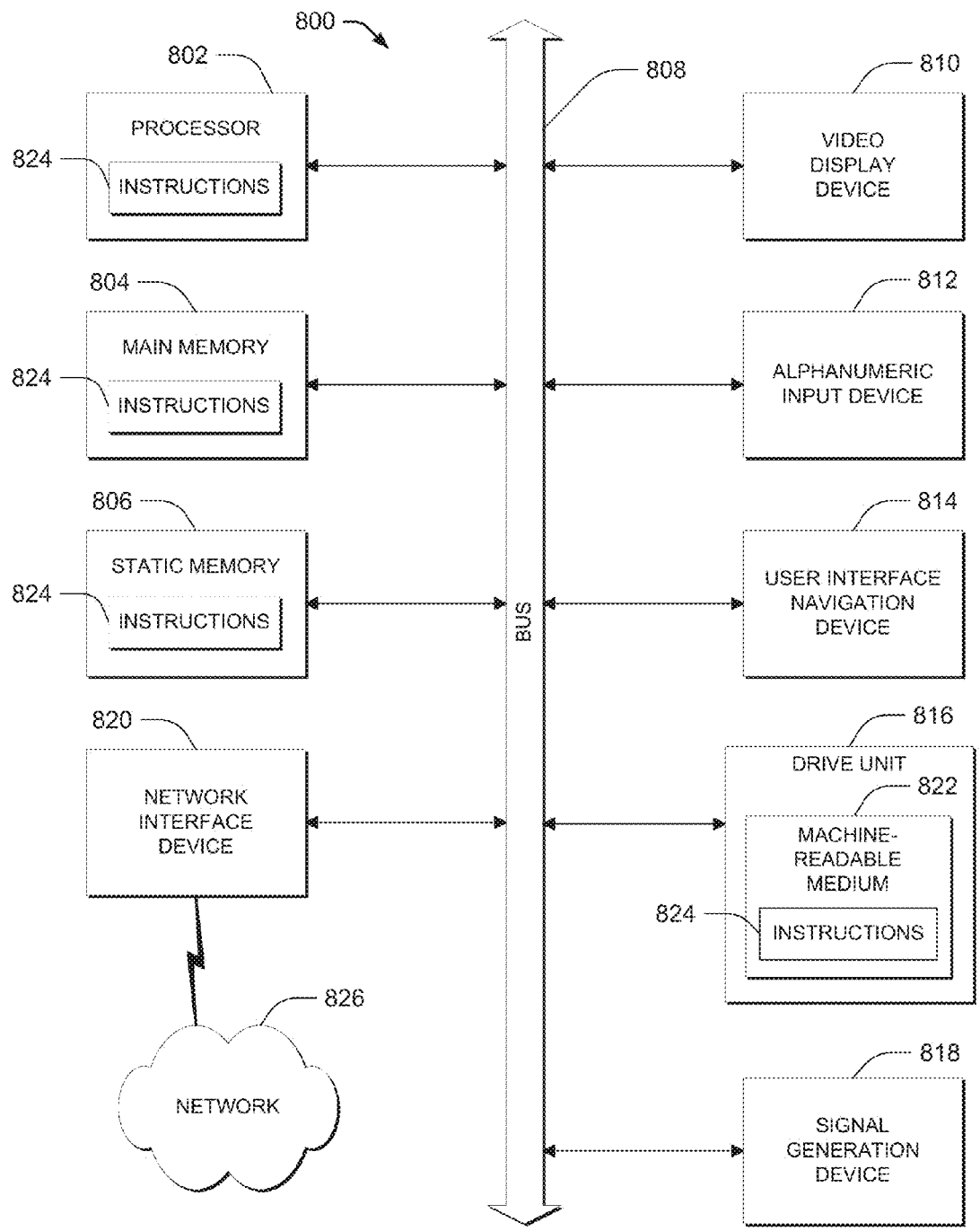
FIG. 8 is a block diagram of a machine in the example form of a computer system within which a set of instructions, for causing the machine to perform any one or more of the methodologies discussed herein, may be executed, according to some embodiments.

FIG. 8 is a block diagram of a machine in the example form of a computer system 800 within which instructions, for causing the machine to perform any one or more of the methodologies discussed herein, may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 800 includes a processor 802 (e.g., a central processing unit (CPU), a graphics processing unit (GPU) or both), a main memory 804, and a static memory 806, which communicate with each other via a bus 808. Computer system 800 may further include a video display device 810 (e.g., a liquid crystal display (LCD) or a cathode ray tube (CRT)). Computer system 800 also includes an alphanumeric input device 812 (e.g., a keyboard), a UI navigation device 814 (e.g., a mouse or touch sensitive display), a disk drive unit 816, a signal generation device 818 (e.g., a speaker) and a network interface device 820.

Disk drive unit 816 includes a machine-readable medium 822 on which is stored one or more sets of instructions and data structures (e.g., software) 824 embodying or utilized by any one or more of the methodologies or functions described herein. Instructions 824 may also reside, completely or at least partially, within main memory 804, within static memory 806, and/or within processor 802 during execution thereof by computer system 800, main memory 804 and processor 802 also constituting machine-readable media.

While machine-readable medium 822 is shown in an example embodiment to be a single medium, the term "machine-readable medium" may include a single medium or multiple media (e.g., a centralized or distributed database, and/or associated caches and servers) that store the one or more instructions 824 or data structures. The term "machine-readable medium" shall also be taken to include any tangible medium that is capable of storing, encoding or carrying instructions (e.g., instructions 824) for execution by the machine and that cause the machine to perform any one or more of the methodologies of the present technology, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and CD-ROM and DVD-ROM disks.

Instructions 824 may further be transmitted or received over a communications network 826 using a transmission medium. Instructions 824 may be transmitted using network interface device 820 and any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., WiFi and WiMAX networks). The term "transmission medium" shall be taken to include any intangible medium that is capable of storing, encoding or carrying instructions for execution by the machine, and includes digital or analog communications signals or other intangible media to facilitate communication of such software.

Although the inventive subject matter has been described with reference to specific example embodiments, it will be evident that various modifications and changes may be made to these embodiments without departing from the broader spirit and scope of the technology. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method comprising:
    displaying a resource associated with a study, the resource comprising a material subject to eye tracking analysis;
    receiving, at a computing device, an image depicting a portion of a user, the image captured while displaying the resource and including reflections caused by light reflected from the user;
    detecting one or more eye features associated with an eye of the user including detecting the one or more eye features using the reflections;
    determining, using the one or more eye features, point of regard information associated with the resource, the point of regard information indicating a location on a display of the computing device at which the user was looking when the image of the portion of the user was taken;
    capturing study data while displaying the resource, the study data comprising data selected from the group consisting of screen capture, blink rate, and mouse data;
    presenting a calibration interface after displaying the resource, the calibration interface including one or more calibration points to calculate an accuracy of user calibration for determining the point of regard information;
    determining, based on the accuracy of user calibration, an accuracy value for the resource associated with the point of regard information; and
    sending the point of regard information in association with the study data and the accuracy value to a server, the server configured to provide the point of regard information and the associated study data and accuracy value to a second user for data analysis.

2. The method of claim 1, wherein the image was taken by a camera located on an eye tracking device coupled to the computing device.

3. The method of claim 1, wherein the light reflected from the user was emitted from one or more light sources located on an eye tracking device coupled to the computing device.

4. The method of claim 1, wherein the resource is one of an image, a video, a website, or a game.

5. The method of claim 1, wherein the point of regard information, the study data, and the accuracy value are accessed from the server by a second user, and wherein the second user subsequently performs an analysis of the point of regard information, the study data, and the accuracy value.

6. The method of claim 1, further comprising:
    determining that the accuracy value is insufficient;
    in response to the determination that the accuracy value is insufficient, presenting the calibration interface after displaying a second resource to perform an updated calibration; and
    updating the accuracy value based on one or more eye features detected during the presentation of the calibration interface.

7. The method of claim 1, wherein the data analysis comprises filtering point of regard information collected from one or more users based at least in part on the accuracy value associated with the point of regard information.

8. A non-transitory machine-readable storage medium storing instructions which, when executed by one or more processors, cause the one or more processors to perform operations comprising:
    displaying a resource associated with a study, the resource comprising a material subject to eye tracking analysis;
    receiving an image depicting a portion of a user, the image captured while displaying the resource and including reflections caused by light with which the user is illuminated and which is reflected from the user;
    detecting one or more eye features associated with an eye of the user including detecting the one or more eye features using the reflections;

determining, using the one or more eye features, point of regard information associated with the resource, the point of regard information indicating a location on a display of the computing device at which the user was looking when the image of the portion of the user was taken;

capturing study data while displaying the resource, the study data comprising data selected from the group consisting of screen capture, blink rate, and mouse data;

presenting a calibration interface after displaying the resource, the calibration interface including one or more calibration points to calculate an accuracy of user calibration for determining the point of regard information;

determining, based on the accuracy of user calibration, an accuracy value for the resource associated with the point of regard information; and sending the point of regard information in association with the study data and the accuracy value to a server, the server configured to provide the point of regard information and the associated study data and accuracy value to a second user for data analysis.

9. The non-transitory machine-readable medium of claim 8, wherein the image was taken by a camera located on an eye tracking device coupled to the one or more processors.

10. The non-transitory machine-readable medium of claim 8, wherein the light reflected from the user was emitted from one or more light sources located on an eye tracking device coupled to the computing device.

11. The non-transitory machine-readable medium of claim 8, wherein the resource is one of an image, a video, a website, or a game.

12. The non-transitory machine-readable medium of claim 8, wherein the point of regard information, the study data, and the accuracy value are accessed from the server by a second user, and wherein the second user subsequently performs an analysis of the point of regard information, the study data, and the accuracy value.

13. The non-transitory machine-readable medium of claim 8, wherein the one or more processors further perform operations comprising:

determining that the accuracy value is insufficient;

in response to the determination that the accuracy value is insufficient, presenting the calibration interface after displaying a second resource to perform an updated calibration; and updating the accuracy value based on the one or more eye features detected during the presentation of the calibration interface.

14. A system, comprising:
a memory that stores instructions and;
one or more processors configured by the instructions to perform operations comprising:

displaying a resource associated with a study, the resource comprising a material subject to eye tracking analysis;

receiving an image depicting a portion of a user, the image captured while displaying the resource and including reflections caused by light with which the user is illuminated and which is reflected from the user;

detecting one or more eye features associated with an eye of the user including detecting the one or more eye features using the reflections;

determining, using the one or more eye features, point of regard information associated with the resource, the point of regard information indicating a location on a display of the computing device at which the user was looking when the image of the portion of the user was taken;

capturing study data while displaying the resource, the study data comprising data selected from the group consisting of screen capture, blink rate, and mouse data;

presenting a calibration interface after displaying the resource, the calibration interface including one or more calibration points to calculate an accuracy of user calibration for determining the point regard information;

determining, based on the accuracy of user calibration, an accuracy value for the resource associated with the point of regard information; and sending the point of regard information in association with the study data and the accuracy value to a server, the server configured to provide the point of regard information and the associated study data and accuracy value to a second user for data analysis.

15. The system of claim 14, wherein the image was taken by a camera located on an eye tracking device coupled to the one or more processors.

16. The system of claim 14, wherein the light reflected from the user was emitted from one or more light sources located on an eye tracking device coupled to the computing device.

17. The system of claim 14, wherein the resource is one of an image, a video, a website, or a game.

18. The system of claim 17, wherein the user information includes each of the screen capture, the blink rate, and the accuracy.

19. The system of claim 14, wherein the point of regard information, the study data, and the accuracy value are capable of being accessed from the server by a second user, and wherein the second user subsequently performs an analysis of the point of regard information, the study data, and the accuracy value.

* * * * *